(12) United States Patent
Konrad

(10) Patent No.: US 7,118,538 B2
(45) Date of Patent: Oct. 10, 2006

(54) HOLDING DEVICE FOR A MEDICAL DEVICE

(75) Inventor: Franz Konrad, Oberndorf bei Schwanenstadt (AT)

(73) Assignee: Greiner Bio-One GmbH, Kremsmünster (AT)

( * ) Notice: Subject to any disclaimer, the term of this patent is extended or adjusted under 35 U.S.C. 154(b) by 183 days.

(21) Appl. No.: 10/894,207

(22) Filed: Jul. 19, 2004

(65) Prior Publication Data

US 2006/0015037 A1  Jan. 19, 2006

(51) Int. Cl.
*A61B 5/00* (2006.01)
*B65D 81/00* (2006.01)

(52) U.S. Cl. ..................................................... 600/576
(58) Field of Classification Search ................ 600/573, 600/576, 577, 581; 604/403, 412, 415, 192; 215/355, 390, 43, DIG. 3
See application file for complete search history.

(56) References Cited

U.S. PATENT DOCUMENTS

| | | | |
|---|---|---|---|
| 4,166,450 A | 9/1979 | Abramson | |
| 4,312,362 A | 1/1982 | Kaufman | |
| 4,333,478 A | 6/1982 | Krieg | |
| 4,378,812 A | 4/1983 | Sarstedt | |
| 4,819,659 A | 4/1989 | Sitar | |
| 5,090,420 A | 2/1992 | Nielsen | |
| 5,275,299 A | 1/1994 | Konrad et al. | |
| 5,294,011 A | 3/1994 | Konrad et al. | |
| 5,297,561 A * | 3/1994 | Hulon | 600/577 |
| 5,495,958 A | 3/1996 | Konrad et al. | |
| 5,505,721 A | 4/1996 | Leach et al. | |
| 5,522,518 A | 6/1996 | Konrad et al. | |
| 5,897,508 A | 4/1999 | Konrad | |
| 6,974,423 B1 * | 12/2005 | Zurcher | 600/576 |
| 6,991,608 B1 * | 1/2006 | Young et al. | 600/581 |

FOREIGN PATENT DOCUMENTS

| | | |
|---|---|---|
| EP | 0 106 290 A2 | 10/1983 |
| EP | 0 286 087 A2 | 10/1988 |
| EP | 0 323 903 A1 | 1/1989 |
| EP | 0 364 777 A1 | 4/1990 |
| EP | 0 489 977 A1 | 12/1990 |
| EP | 0 478 459 A1 | 9/1991 |
| WO | WO 88/04154 | 6/1988 |
| WO | WO 89/10723 | 11/1989 |
| WO | WO 92/04867 | 4/1992 |

* cited by examiner

*Primary Examiner*—Max F. Hindenburg
*Assistant Examiner*—Brian Szmal
(74) *Attorney, Agent, or Firm*—Collard & Roe, P.C.

(57) ABSTRACT

A holding device (1) for assembling a medical device with a receiving vessel (2) and a holder (3) for a cannula (11), directed towards an open front end (6) of the receiving vessel (2). A flow-through bore of the cannula (11) is connected by a connecting passage (22) between the holder (3) and a front wall (8) of the receiving vessel (2), incorporating a flow passage (21) of a holding part (20) arranged eccentrically with respect to a longitudinal axis (5) of a receiving chamber (9) of the receiving vessel (2). Disposed between the connecting passage (22) and the receiving chamber (9) is an openable hose valve (15). Disposed on the jacket portion (4) of the receiving vessel (2) is a first connecting part (23), whilst a second connecting part (24) is disposed on a support part (14) of the holder (3). A continuous circumferential gas-tight and liquid-proof joint is provided between the holder (3) and the receiving vessel (2).

25 Claims, 7 Drawing Sheets

HOLDING DEVICE FOR A MEDICAL DEVICE

BACKGROUND OF THE INVENTION

1. Field of the Invention

The invention relates to a holding device for assembling a medical device, of the type used to take samples of bodily fluids, such as blood, urine, etc., and also for removing samples from containers needed for administering serum, plasma or medical substances.

2. The Prior Art

A holding device for a blood sample tube of a blood sample device is well known from patent specification U.S. Pat. No. 5,897,508 A, for example, which has a receiving vessel for a front end of the blood sample tube, sealed by a closure device, incorporating a needle holder. A cannula is mounted in the needle holder, directed towards the open front end of the receiving vessel, and projects in the direction thereof. A through-flow opening communicates via a connecting passage disposed between the needle holder and an end wall of the receiving vessel, with a sample needle of a needle assembly, disposed eccentrically with respect to a central longitudinal axis of the receiving chamber. Disposed between the connecting passage and a receiving chamber of the receiving vessel is a valve arrangement which can be opened as and when necessary. This valve arrangement incorporates a hose valve or flap valve disposed between the cannula and the receiving chamber and/or connecting passage. The cannula is preferably disposed concentrically with the receiving vessel. A through-flow passage opens between the cannula and an outer wall of the receiving vessel into the connecting passage. The disc-shaped support part has a periphery with an annular collar projecting out therefrom towards the end wall of the receiving vessel and the collar has an end surface connected to a peripheral bearing surface of the front wall of the receiving vessel in a gas-tight and liquid-proof manner by means of a continuous weld seam.

Other holding devices for blood sample tubes of a blood sample device are known from patent specification WO 89/10723 A1, for example, which has a receiving vessel for a front end of the blood sample tube. The blood sample tube is closed at its front end by a closure device. The receiving vessel is provided with a needle holder for a cannula and projects in the direction of an open front end of the receiving vessel, the through-opening of which is connected to a sample needle of a needle assembly via a connecting passage disposed between the needle holder and the end wall of the receiving vessel. This sample needle is disposed eccentrically with respect to a central longitudinal axis of the receiving chamber. Between the connecting passage and a receiving chamber of the receiving vessel, a valve arrangement is provided which can be opened as and when required. This valve arrangement comprises the cannula and the needle holder. The cannula is mounted so as to be adjustable in the lengthways direction of the central longitudinal axis of the receiving vessel in a bore of the needle holder. To restrict the adjusting movement, the cannula has a stop projecting out in a radial direction from the outer periphery at its end disposed in the connecting passage. This being the case, the cannula is squeezed together at its end facing the connecting passage and is bent around through 90 degrees and has an opening in the side wall through which the through-flow opening establishes a flow communication with the connecting passage. A disadvantage of this arrangement is the fact that the cannula is displaceably mounted in the needle holder, which makes it difficult to achieve a gas-tight seal between the sample needle and the blood sample tube, and in addition to permeability, which to a certain extent also leads to some leakage of blood, the vacuum of the blood sample tube can not be deployed for taking the blood sample in many cases.

Other blood sample devices are known from U.S. Pat. No. 4,819,659 A, European applications 0 478 459 A1, 0 286 087 A2 and 0 364 777 A1, in which the cannula in each case is of a continuous design and is mounted in a needle holder or in a guide sleeve. This being the case, the cannula simultaneously constitutes the sample needle at one end and the needle used to puncture the closure plug of the blood sample tube at the other end. In addition, at the end facing the blood sample tube, the cannula is surrounded by a valve arrangement in the form of a hose valve, which can be opened as and when required. In these embodiments of the sample device, it is not possible to separate the holding device from the needle assembly, for example in order to be able to administer an infusion to the patient, without having to remove the needle. Furthermore, an increased safety risk exists for the user because the sample needle is already fixed and injuries can already occur during preparation of the holding device. Another disadvantage is the fact that the sample needle, which is of a continuous design, is disposed centrally with respect to the holding device, as a result of which the entire sample device has to be inclined to a greater degree when piercing the vein, thereby increasing the risk of injury.

SUMMARY OF THE INVENTION

The underlying objective of the present invention is to propose a reliable and above all tightly sealed join between the receiving vessel and the holder, in particular the holder part, which is simple and inexpensive to manufacture.

This objective is achieved by the invention by means of a holding device incorporating a receiving vessel with a jacket portion with a longitudinal axis and one open end, in which a front wall closes off an end of the receiving vessel at the end lying opposite the open end, and the jacket portion and front wall define a receiving chamber. Disposed on the jacket portion close to the front wall is a first connecting part, which projects out from the jacket portion in the direction towards the longitudinal axis and extends continuously around the periphery. A holding part is connected to the front wall of the receiving vessel and projects out from it in a direction remote from the jacket portion, the holding part being arranged eccentrically with respect to the longitudinal axis and defining a flow passage. One end of a cannula faces the front wall of the receiving vessel and an opposite end faces the open end of the receiving vessel, the cannula defining a flow-through bore. A holder for the cannula comprises a support part with a periphery, directed towards the jacket portion of the receiving vessel, and a support holding the cannula in a fixed position in a gas-tight and liquid-proof manner, the opposite end of the cannula projecting beyond the support so that the support part of the holder and the front wall of the receiving vessel define an inter-connecting passage, with the connecting passage establishing a flow connection via the passage of the holding part to the flow-through bore of the cannula. Another connecting part is also provided and extends around the periphery of the support part, which is designed to connect the first connecting part to the receiving vessel. At least one of the connecting parts is provided with means, which means are designed to direct the energy needed to produce the continuous, peripheral gas-tight and liquid-proof join between the holder and the receiving vessel. A valve arrangement which can be selectively opened is disposed between the connecting passage and receiving chamber, said valve arrangement comprising a hose valve disposed between the cannula and the receiving chamber.

The advantage of this is that, firstly, the disposition of the two connecting parts enables the connecting region between the receiving vessel and the support part to be definitively fixed in terms of position and, in addition, the means provided directing energy results in a deflection or orientation of the energy used for the process of fusing the material or substance of the connecting parts so that the joining process can be better controlled and more reliably operated. The disposition in the outer peripheral region means that a peripheral gas-tight and liquid-proof connection is obtained between the receiving vessel, in particular its jacket portion, and the support part of the holder by the two connecting parts in conjunction with the energy directing means. Depending on the disposition and design of the connecting parts, an adequate connecting region is obtained as viewed in the direction of the longitudinal axis, which can be easily controlled by the production machinery, thereby reducing manufacturing costs.

However, it is also of advantage if the energy directing means is provided in the form of converging boundary surfaces which terminate in a body edge, because this approach produces a predefined region in which the joining process can take place, is defined exactly from the outset and can be unambiguously set in terms of its positioning. The boundary surfaces terminating in the body edge may also be used as a means of pre-centring and positioning the components which have to be joined to one another.

It is also of advantage if the boundary surfaces subtend an angle that is equal to or less than 90°. The choice of angle for the converging boundary surfaces produces a directed flow of energy in the joining material needed for the fusing process which is more effectively concentrated in the region of the body edge, thereby ensuring that the joining process is more reliable and in particular produces a more efficient seal.

It is also of advantage if one of the boundary surfaces of the energy directing means extends parallel with the longitudinal axis, because this enables the components which have to be joined to one another to be pre-positioned in the region of these boundary surfaces and coaxially aligned with one another.

In another embodiment, the other boundary surface of the energy directing system is oriented at an angle to a plane extending perpendicular to the longitudinal axis, which is of advantage because it also permits pre-positioning of the components to be joined to one another in the direction of the longitudinal axis and, if the receiving vessel is placed upright with the open end at the top, the holder to be joined to it merely has to be inserted in the receiving chamber, in which case the holder can be inserted as far as the boundary surface serving as a stop surface.

Another option is to provide the energy directing means on the first connecting part, in which case the fusing process needed to produce the join takes place as a result of the energy flow concentrated in the region of the first connecting part disposed in the receiving vessel.

It is also possible for the inclined boundary surface on the first connecting part to extend at an angle from the jacket portion in the direction towards the longitudinal axis and, starting from the jacket portion, a distance from the front wall then becomes greater, the greater the distance is in the direction towards the longitudinal axis. As a result of the angled, increasing boundary surface in the direction towards the receiving chamber, the body edge projects at its widest point in the direction of the open end of the vessel and thus forms the first stop edge or surface for the other connecting part of the holder, so that the proportion of material of the connecting part on the receiving vessel becomes larger, the greater the distance to the front wall is.

In another embodiment, the first connecting part on the receiving vessel is provided in the form of a hollow cylindrical body and is moulded on the jacket portion, the advantage of which is that a specific quantity of fusing material can be provided for the joining process from the outset and the position of the joint between the components to be joined can be defined beforehand.

Another possibility is for the second connecting part to be disposed circumferentially on an outer periphery of the support part, because this will also enable a peripheral pre-definable connecting region on the support part to be obtained, producing a perfect joint with the receiving vessel in the region of its jacket portion.

Accordingly, another embodiment is possible in which the second connecting part is formed by the support part, which means that an integrally manufactured component made from a uniform material can be obtained in which the joint region can be exactly determined from the outset.

Another option is for the energy directing means to be disposed on the second connecting part, in which case the start or beginning of the fusing process is shifted to the region of the holder, thereby enabling the position of the joint region between the two components to be connected to be exactly determined beforehand.

In another embodiment, one of the boundary surfaces is inclined at an angle to the plane disposed perpendicular to the longitudinal axis and the inclination starting from the outer periphery of the second connecting part in the direction towards the holder is oriented for receiving the cannula. On the one hand, this enables an exact lengthways positioning of the two components to be joined to one another and, on the other hand, it also shifts the start of the fusing process towards the connecting part disposed on the holder.

In one advantageous embodiment, a collar, particularly of a circular shape, is provided on the support part, projecting out from the support part in the direction remote from the holder for the cannula, which, firstly, provides an additional means of coaxially aligning the parts to be joined to one another before the start of the joining process and, secondly, provides a stop boundary for producing the connecting passage to be formed between the front wall and the support part during the joining process.

Another possibility is to provide an end surface of the collar at a distance from the front wall of the receiving vessel in the mutually joined position because this provides a reserve path for the joining process as the plastic material melts, but a minimum distance can still be maintained for forming the connecting passage under all circumstances.

In another embodiment, when the components to be connected are in the de-moulded loose state, the two connecting parts, as viewed in their cross section, overlap with one another, as a result of which the joint region of the components to be joined to one another is shifted to the region of the peripheral jacket portion of the receiving vessel, thereby providing a larger amount of material for producing the join layer, in particular the weld seam between the components to be joined.

In another embodiment, a height of the collar projecting beyond the second connecting part in the direction parallel with the longitudinal axis is shorter than a height extension of the first connecting part in the same direction, which means that the holder can be held pre-positioned at a pre-definable distance from the front wall prior to making the joint, making sufficient joining space free during the joining process to enable the holder to be inserted in the direction towards the front wall.

In another option, the collar has an external dimension which is the same as or slightly smaller than an internal clearance width of the first connecting part, providing an easy means of coaxially aligning the two components to be joined to one another in readiness for the joining process.

Another possibility is to provide at least one stop element on the support element projecting out in the direction towards the longitudinal axis, which enables the path to be restricted when the components to be joined to one another are inserted during the joining process and guarantees that the connecting passage will be the correct size.

Another possibility is to provide the peripheral gas-tight and liquid-proof joint between the two connecting parts in the form of a weld seam, which means that the peripheral gas-tight and liquid-proof joint can be produced inexpensively without the need for any additional means or materials.

It is also of advantage if the weld seam is produced by a thermal joining process selected from the group consisting of ultrasound welding, high-frequency welding or vibration welding, because the welding principle used enables better account to be taken of the material used. The welding process can also be more easily controlled and the weld depth better influenced.

The receiving vessel, holder and connecting parts may be made from a plastic material, because this will mean that components can be made easily and above all inexpensively by a production process which is reproducible, such as possible in the case of an injection moulding process.

It is also of advantage if the plastic material is selected from the group consisting of polypropylene (PP), polystyrene (PS), polycarbonate (PC), because this means that a material can be used which can be melted and then subsequently re-softened, thereby guaranteeing a reliable and above all gas-tight and liquid-proof joint.

It is also possible for the retaining part to be provided with a Luer cone on at least certain regions of its external surface because this will provide an easy way of enabling components such as needles or similar to be coupled easily and as standard with the holding device.

However, the holding part could also be of a tubular shape in at least certain regions of its external surface since this will facilitate penetration of a membrane, enabling other medical components such as blood bags or similar to be connected to the holding device.

Finally, at least one stop element may be provided in the receiving chamber in the section of the holder facing the region of the open end of the receiving vessel, to co-operate with a sample tube disposed on the jacket portion which can be inserted in the receiving chamber, thereby providing a stop boundary to restrict or determine the insertion path and thus ensure that pressure forces in the direction of the longitudinal axis are not introduced directly into the holder for the cannula but, instead, these forces are transmitted to the receiving vessel due to an abutment on the stop elements having been effected beforehand.

BRIEF DESCRIPTION OF THE DRAWINGS

The invention will be described in more detail below with reference to the appended drawings illustrating examples of embodiments.

DETAILED DESCRIPTION OF PREFERRED EMBODIMENTS

Figure 1:
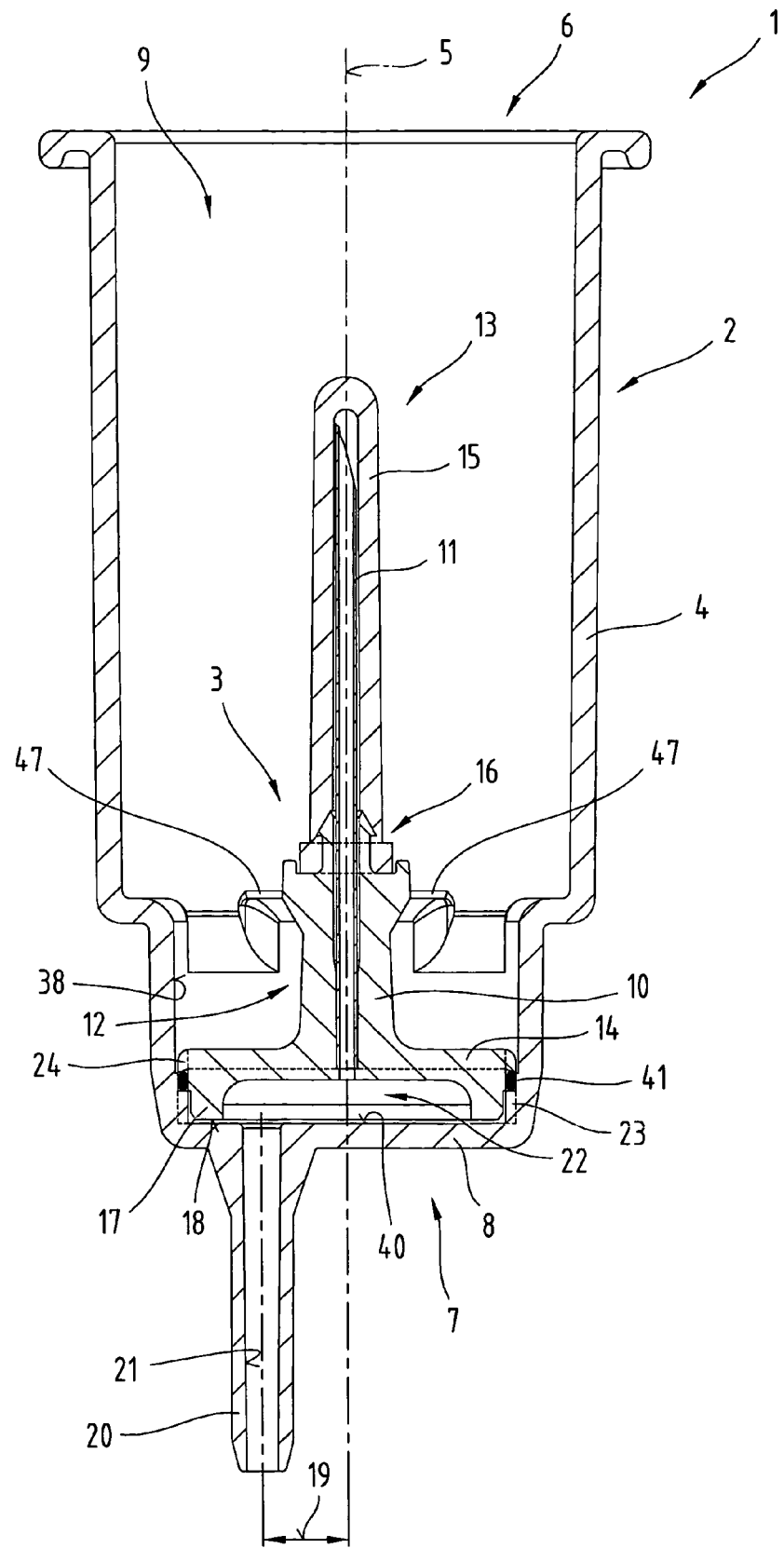
FIG. 1 is a simplified, schematic diagram showing a side view, in section, of a holding device as proposed by the invention with a receiving vessel and a holder with a cannula, in the mutually connected position.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc,. relate to the drawing specifically being described and can be transposed in terms of meaning to a new position when another position is being described. Individual features or combinations of features from the different embodiments illustrated and described may be construed as independent inventive solutions or solutions proposed by the invention in their own right.

The embodiments illustrated as examples show possible design variants of the holding device and it should be pointed out at this stage that the invention is not restricted to the design variants specifically illustrated but also encompasses various combinations of the individual design variants with one another, and these possible variations will be within the reach of the person skilled in this technical field on the basis of the technical teaching of the invention. Accordingly, all conceivable design variants which can be obtained by combining individual features of the described and illustrated embodiments are possible and are included within the scope of the invention.

Figure 2:
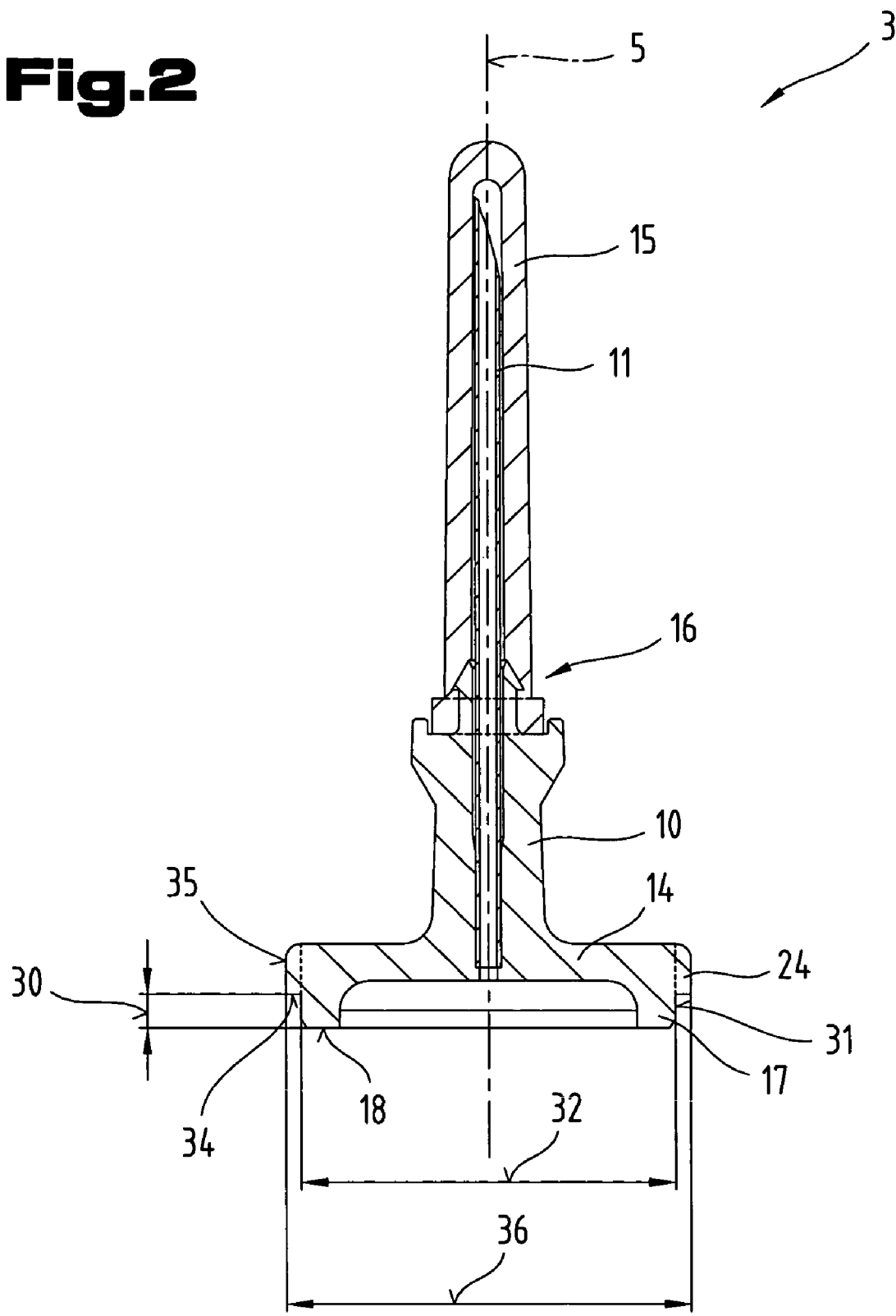
FIG. 2 is a simplified, schematic diagram showing a side view, in section, of the holder illustrated in FIG. 1 prior to connection with the receiving vessel.
Figure 3:
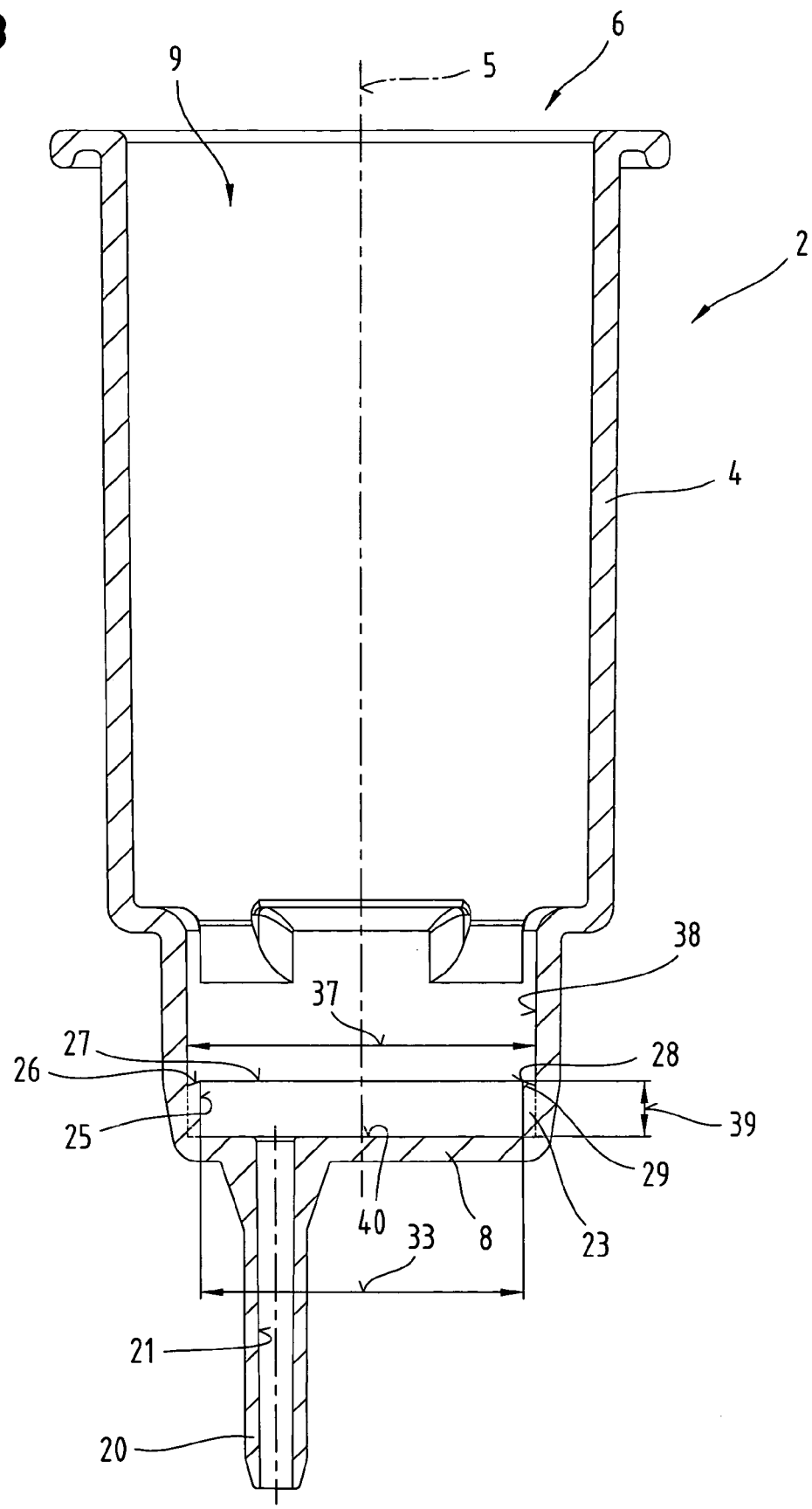
FIG. 3 is a simplified, schematic diagram showing a side view, in section, of the receiving vessel illustrated in FIG. 1 prior to connection with the holder.

FIGS. 1 to 3 illustrate one possible embodiment of a holding device 1 for assembling a medical device, incorporating a receiving vessel 2 and a holder 3 disposed therein. The holding device 1 may be part of a blood sampling device, for example, used in conjunction with a blood sample tube, which is generally known and not illustrated in detail, with a cannula and Luer cone for taking blood samples from the veins or may be used in conjunction with ready filled bags or similar as a means of drawing off samples of their contents. This might be a blood bag with a connecting hose, for example, in which case one end of the hose is connected to the interior of the bag and the other end is connected to the receiving vessel 2.

In this particular example, the receiving vessel 2 preferably has a cylindrical or virtually cylindrical jacket portion 4 with ends 6, 7 spaced apart from one another in the direction of a longitudinal axis 5. In this case, the first end 6 is open and the other end 7 is closed off by a front wall 8 disposed perpendicular to the longitudinal axis 5. This being the case, the jacket portion 4 and the front wall 8 enclose a receiving chamber 9. If the holding device 1 is used as part of a blood sampling device, the open end 6 is used for inserting a blood sample tube, not illustrated, incorporating, in a known manner, a container with a seal at one end which can be pierced, which may be of the type disclosed in patent specifications U.S. Pat. No. 5,275,299 A, U.S. Pat. No. 5,495,958 A, U.S. Pat. No. 5,522,518 A or U.S. Pat. No. 5,294,011 A.

As also illustrated, the holder 3 also has a support 10 for a cannula 11 which is fixedly retained therein. The cannula 11 is secured in the support 10 so that it is immobilised and is gas-tight and liquid-proof. This may be accomplished, for example, by moulding the cannula 11 and the holder 3, in particular the support 10, integrally in a single work process, for example by an integral injection process. However, it would also be possible for the cannula 11 to be secured in the support 10 in a gas-tight and liquid-proof manner by a subsequent joining process, for example by means of a bonding or welding process. The cannula 11 has a first end 12 directed towards the front wall 8 of the receiving vessel 2 and another end 13 opposite it, facing the open end 6 or open end face of the receiving vessel 2, so that the cannula 11 forms a through-flow orifice. The holder 3 for the cannula 11 in the embodiment described as an example here incorporates the support 10 for the cannula 11, a support part 14 joined thereto and the cannula 11. The end 13 of the cannula 11 facing the open end 6 is covered by a valve arrangement which can be operated and opened in a known manner and in this particular example by a hose valve 15. This stocking-type hose valve 15 is preferably provided in the form of an elastic, liquid-proof protective cover, e.g. made from a highly elastic, self-closing silicone rubber, a synthetic rubber or similar.

In the region facing the open end 6 of the receiving vessel 2, the support 10 of the holder 3 has a holding device 16 for holding the open end of the hose valve 15 open, in which case the holding device 16 is provided in the form of a peripheral retaining lug projecting out from the support 10 and tapering in a conical arrangement in the direction towards the open end 6 of the receiving vessel 2. The conical taper or narrowing, or conical widening if viewed in the direction in which the hose valve 15 is inserted, facilitates the insertion process in terms of getting past the retaining surface projecting out from the support 10 formed by the retaining lug and disposed perpendicular to the longitudinal axis 5. The open end of the highly elastic hose valve 15 contracts behind the retaining surface, conforming to the diameter of the support 10, thereby ensuring that the hose valve 15 is secured to prevent it from being unintentionally pulled off the holding device 16.

The support part 14 of the holder 3 in the embodiment illustrated as an example here is a disc-shaped component, the outer peripheral circumferential region of which is directed towards the jacket portion 4 of the receiving vessel 2.

In this embodiment, a circular collar 17 is also provided on the support part 14 at the end facing the front wall 8, said collar 17 being disposed on the support part 14 in its outer peripheral region and projecting out from the support part 14 in the direction towards the front wall 8. An end surface 18 of the collar 17 facing the front wall 8, which preferably extends at a right angle to the longitudinal axis 5, delimits the collar in this region.

Disposed at a distance 18 eccentrically from the longitudinal axis 5 is a tubular retaining part 20. In its interior, the retaining part 20 has a flow passage 21. The retaining part 20 connected to the front wall 8 projects out from the front wall 8 in the direction away from the jacket portion 4. The support part 14 and optionally also the collar 17 and front wall 8, also bounds a connecting passage 22, into which the flow passage 21 of the retaining part 20 opens. Consequently, the flow passage 21 extends through the front wall 8 and thus opens into the connecting passage 22. The flow orifice inside the cannula 11 is also in flow communication with the connecting passage 22, thereby establishing an end to end connection, starting from the flow passage 21 via the connecting passage 22 and through to the end 13 of the cannula 11 closed off by the hose valve 15.

As also illustrated in a simplified manner in FIG. 1, a first connecting part 23 is disposed in the receiving chamber 9 close to the front wall 8 on the jacket portion 4, projecting out from the jacket portion 4 in the direction towards the longitudinal axis 5 and extending continuously around the periphery. Another connecting part 24 is provided around the periphery of the support part 14, designed to connect with the first connecting part 23 on the receiving vessel 2.

The receiving vessel 2 illustrated in FIG. 3 is shown in the state before the holder 3 is inserted and in its de-moulded state prior to being connected to it by a process that will be described in more detail below, the disposition and design of the first connecting part 23 being an important factor in obtaining a perfect join with the other connecting part 24 of the holder 3 in the embodiment illustrated as an example here. In the particular embodiment illustrated, the first connecting part 23 on the receiving vessel 2 is provided in the form of a hollow cylindrical body, which is moulded or formed on the jacket portion 4 at the end facing the receiving chamber 9. This connecting part 23 extends from the front wall 8 towards the open end 6 of the receiving vessel 2 and its external shape at the end facing the receiving chamber 9 is determined by boundary surfaces 25, 26. One of the two boundary surfaces, in this particular embodiment boundary surface 25, extends parallel with the longitudinal axis, whilst the other boundary surface—in this particular embodiment boundary surface 26—is inclined at an angle to a plane 27 disposed perpendicular to the longitudinal axis 5.

The inclined boundary surface 26 of the first connecting part 23 is angled in the direction towards the longitudinal axis 5 starting from the jacket portion 4, so that, starting from the jacket portion 4, a distance to the front wall 8 becomes larger at an increasing distance towards the longitudinal axis 5. These two converging boundary surfaces 25, 26 terminate in a body edge 28 and the angle subtended by the boundary surfaces 25, 26 is equal to or smaller than 90°. It has proved to be of advantage to opt for an angular range of between 10° and 80°, preferably 70°. The smaller the selected angle, the more acutely the boundary surfaces 25, 26 will converge with one another. The choice of angle will depend on the material of the parts to be connected to one another, the mass of the fusible material and the power or energy density applied for the purposes of the joining process. This body edge 28 constitutes a means for the joining process and serves as an energy directing means 29, enabling the process of fusing the material to be defined exactly beforehand. The weld seam for joining the two components is produced by a thermal joining process selected from the group consisting of ultrasound welding, high-frequency welding or vibration welding, since this will be an advantage in terms of securing the best and possibly least expensive means of obtaining the desired welding result.

In the case of ultrasound welding, the molecules are caused to vibrate by a so-called sonotrode and the internal friction will generate the heat needed for the fusing process, thereby enabling the associated welding process to proceed in a simple and above all reliable manner. The body edge 28 with its preferably acute-angled design is the first to melt and promotes the rest of the joining process and the formation of the gas-tight and liquid-proof joint.

If using ultrasound welding for the welding process, the energy flow from the applied energy is concentrated, which enables a very high density of energy to be obtained in the region of the body edge 28, thereby causing it to melt and assist the associated welding process in a simple and above reliable manner. In the embodiment illustrated as an example here, the energy directing means 29 is provided on the first connecting part 23 by means of the two boundary surfaces 25, 26 and the body edge 28.

FIG. 2 provides a simple illustration of the holder 3 used to assemble the holding device 1, again in its de-moulded initial state before the process by which it is joined to the 2. As may be seen, the second connecting part 24 is provided on the support part 14 in the region of its outer periphery, also extending circumferentially around the entire periphery of the support part 14 or support 10. However, it would also be possible for the second connecting part 24 to be provided directly by means of the support part 14 itself. The connecting part 24 is illustrated in a schematic simplified form by a broken line, extending flush with the outer delimiting ends of the collar 17 and parallel with the longitudinal axis 5.

As may be seen from comparing FIGS. 2 and 3, a height 30 of the collar 7 projecting out from the second connecting part 24 in the direction parallel with the longitudinal axis 5 is shorter than a height of the first connecting part 23—in this case between the front wall 8 and the boundary surface 26 or body edge 28—in the same direction. In terms of cross section, the dimensions of the two connecting parts 23, 24 in the plane 27 extending perpendicular to the longitudinal axis 5 are such that when the components to be connected to one another—receiving vessel 2 and holder 3—are in the de-moulded or loose state, the two connecting part 23, 24 overlap with one another in their cross section. An outer delimiting end 31 of the support part 14 and collar 17 is preferably disposed in the direction parallel with the longitudinal axis 5 and its external dimension 32 in the direction perpendicular to the longitudinal axis 5 is the same as or slightly smaller than an internal clearance width 33 of the first connecting part 23 in the same spatial direction. Consequently, the entire holder 3 can be inserted in the receiving chamber 9, in which case the outer delimiting end 31 is preferably disposed in a parallel position within the boundary surface 25 of the first connecting part 23. As a result of the fact that the two connecting parts 23, 24 overlap in cross section in the plane 27 perpendicular to the longitudinal axis 5 as described above, another boundary surface 34 of the second connecting part 24, which in this embodiment is disposed in the direction perpendicular to the longitudinal axis 5, moves into an abutting position in the region of the body edge 28 or boundary surface 26 of the first connecting part 23.

Finally, another boundary surface 35 parallel with the longitudinal axis 5 delimits the second connecting part 24 in the region of its outer circumferential periphery. This outer boundary surface 35 is preferably disposed in a cylindrical arrangement relative to the longitudinal axis 5 and has an external dimension 36, in particular a diameter, that is slightly smaller than an internal clearance width 37 of the jacket portion 4 in the region of its internal surface 38 in the region of the first connecting part 23.

As may best be seen from FIG. 3, the jacket portion 24 in this embodiment becomes narrower along its longitudinal extension, starting from the open end 6 of the receiving vessel 2 through to its closed end 7, and in the region of the smaller dimension, the jacket portion 4 is designed to accommodate the holder 3 and because the external dimension 36 of the second connecting part 24 matches the internal clearance width 37 of the jacket portion 4, the holder 3 can be pre-centred relative to the receiving vessel 2. Accordingly, the external dimension 36, in particular the diameter, is the same as or slightly smaller than the clearance width 37 in the region of the jacket portion 4 adjoining the first connecting part 23 in the direction towards the open end 6. This enables the holder 3 to be circumferentially centred or centrally oriented relative to the longitudinal axis 5 of the receiving vessel 2.

As viewed in the direction of the longitudinal axis 5, as the holder 3 is inserted in the receiving chamber 9, a mutual orientation relative to the longitudinal axis 5 is firstly secured and as the holder 3 is inserted farther in the direction towards the front wall 8, a pre-definable position is obtained whereby the boundary surface 34 of the second connecting part 24 sits on the body edge 28 or boundary surface 26 of the first connecting part 23. In this position, the end surface 18 constitutes the difference between a height extension 39 of the first connecting part 23—starting from a wall surface 40 or internal face of the front wall 8 facing the receiving chamber 9 in the direction towards the longitudinal axis 5 as far as the body edge 28—less the height 30 of the collar 17 projecting above the boundary surface 34. The purpose of this difference is to permit the holder 3 to move during the process by which it is joined to the material of the jacket portion 4 of the receiving vessel 2 in the direction towards the front wall 8 as energy is simultaneously applied for the purpose of the joining process. Consequently, in the mutually joined position, the end surface 18 of the collar 17 is arranged at a distance from the front wall 8, in particular that of the wall surface 40 facing the receiving chamber 9, as schematically indicated in FIG. 1. However, it would also be possible for the holder 3 to move so far in the direction towards the front wall 8 or its wall surface 40 during the joining process that the end surface 18 reaches a position abutting with the wall surface 40 of the front wall 8.

The gas-tight and liquid-proof joint between the two connecting parts 23, 24 illustrated in the simplified schematic diagram of FIG. 1 is shown by a schematically indicated weld seam 41. This weld seam may be produced by a welding process of the type described above. This being the case, the receiving vessel 2 and the holder 3 are made from a plastic material, thereby enabling the two materials to be joined with and to one another to obtain a gas-tight and liquid-proof seal. The plastic material used to make the receiving vessel 2 and holder 3 and the connecting part 23, 24 is selected from the group consisting of polypropylene (PP), polystyrene (PS), polycarbonate (PC). It is of advantage if the material is opaque, see-through or totally transparent.

Depending on the intended purpose of the holding device 1, the retaining part 20 may be of various different designs. In order to pierce a membrane or such like, the retaining part 20 may also be of a tubular shape, at least in certain regions of its outer surface, and the tubular part will extend starting form the end remote from the front wall 8 in the direction towards the front wall 8 and its external dimension will be smaller than the standard Luer cone.

If the holding device 1 is to be used for holding samples of bodily fluids, in particular blood, the retaining part 20 may be designed in the form of a Luer cone in a known manner, at least in certain regions of its external surface. As a result of this embodiment, a needle assembly, not illustrated, can be connected to the retaining part 20, in a generally known manner.

Figure 4:
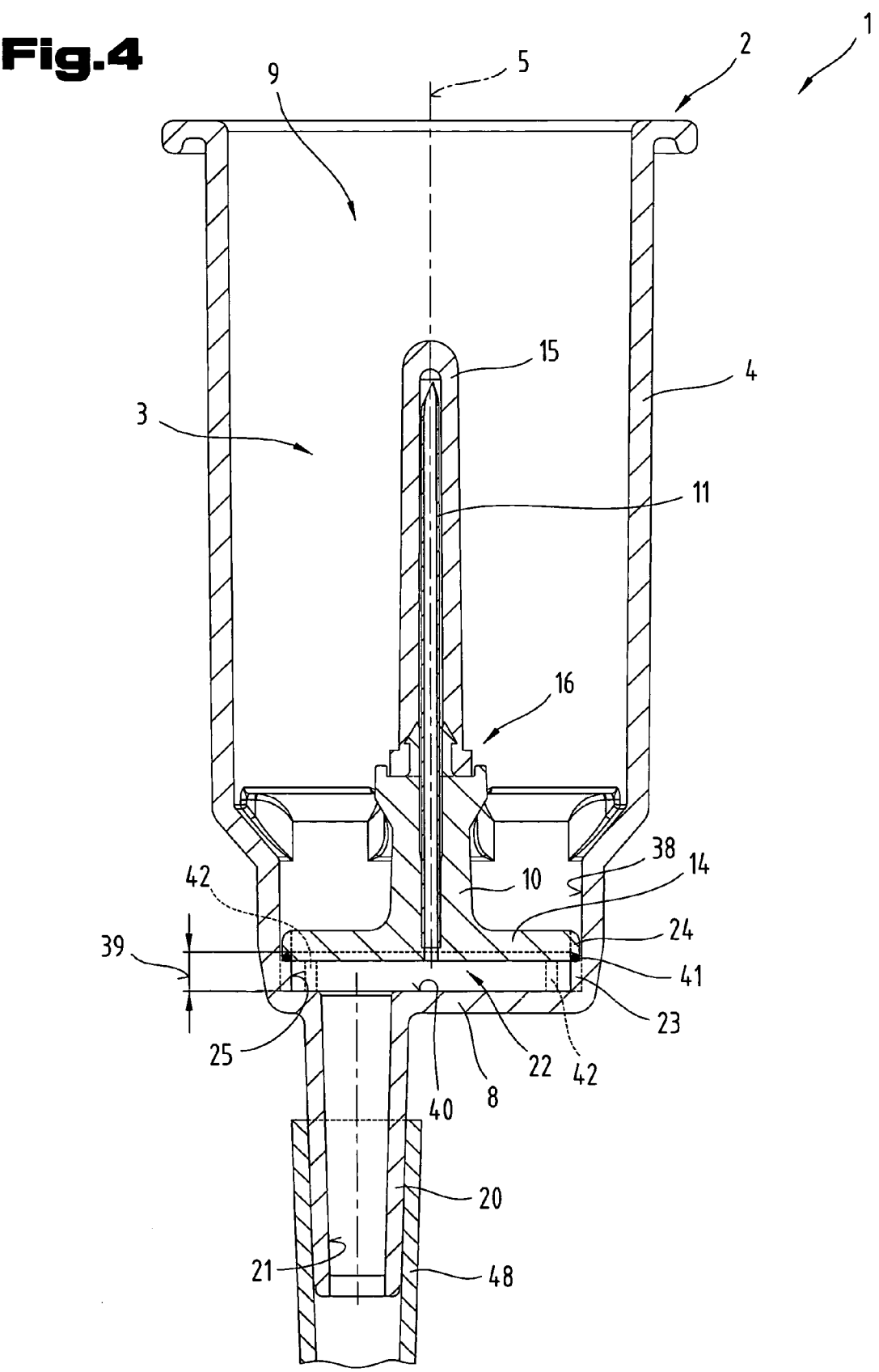
FIG. 4 is a simplified, schematic diagram showing a side view in section of another possible embodiment of the holding device proposed by the invention with a receiving vessel and a holder with a cannula, but without a collar, in the mutually connected position.

FIG. 4 illustrates another possible and optionally independent embodiment of the holding device 1, but to avoid unnecessary repetition, reference may be made to the more detailed description given above with reference to FIGS. 1 to 3. The same parts are indicated by the same names and the same reference numbers as those used for FIGS. 1 to 3. The receiving vessel 2 with its first connecting part 23 is connected to the holder 3, in particular its support part 14, incorporating the second connecting part 24 in the same way as described in detail above with reference to FIGS. 1 to 3.

Unlike the embodiment illustrated and described above, the support part 14 does not have a collar 17 projecting out from it and the holder 3 is initially centred relative to the longitudinal axis 5 due to the co-operation of the internal surface 38 of the jacket portion 4 and the peripheral external boundary surface 35. The holder 3 is supported in the direction of the longitudinal axis 5 by pre-positioning the circular boundary surface 34 on the body edge 28, as described in detail above. The connecting passage 22 linking the flow passage 21 in the retaining part 20 through to the flow orifice inside the cannula 11 is bounded by the front wall 8, in particular the wall surface 40 facing the receiving chamber 9 in this embodiment, preferably the cylindrical boundary surface 25 of the first connecting part 23 and the support part 14 of the holder 3.

In the same way as described above, the retaining part 20 of this embodiment is provided in the form of a Luer cone. Naturally, it would also be possible to provide the retaining part 20 as a cylindrical or tubular part rather than as a Luer cone, in which case it may have only a minimal de-moulding incline in the region of its outer surface.

The embodiment illustrated as an example here does not have any stop restriction of the collar on the wall surface 40 of the front wall other than those described in connection with the embodiments illustrated in FIGS. 1 to 3. Consequently, during the joining process, care must be taken to ensure that the connecting passage 22 is correctly formed, and it will have a larger capacity than in the previous embodiment due to the fact that the circular collar 17 is omitted. In dimensioning and selecting the height extension 39 of the de-moulded first connecting part 23, special attention must be paid to the spacing of the support part 14 from the front wall 8 in order to form the connecting passage 22 on the one hand and on the other hand to ensure that a perfect joining process can be run to form the weld seam 41. However, as indicated by broken lines, it would also be possible to provide at least one but preferably several spacing elements 42 on the support part 14 in order to guarantee the correct spacing of the support part 14 from the wall surface 40 of the front wall 8, thereby ensuring that the connecting passage 22 is of a minimum size in terms of volume. These spacing elements 42 project out from the support part 14 in the direction towards the longitudinal axis 5 in the direction remote from the support 10.

Figure 5:
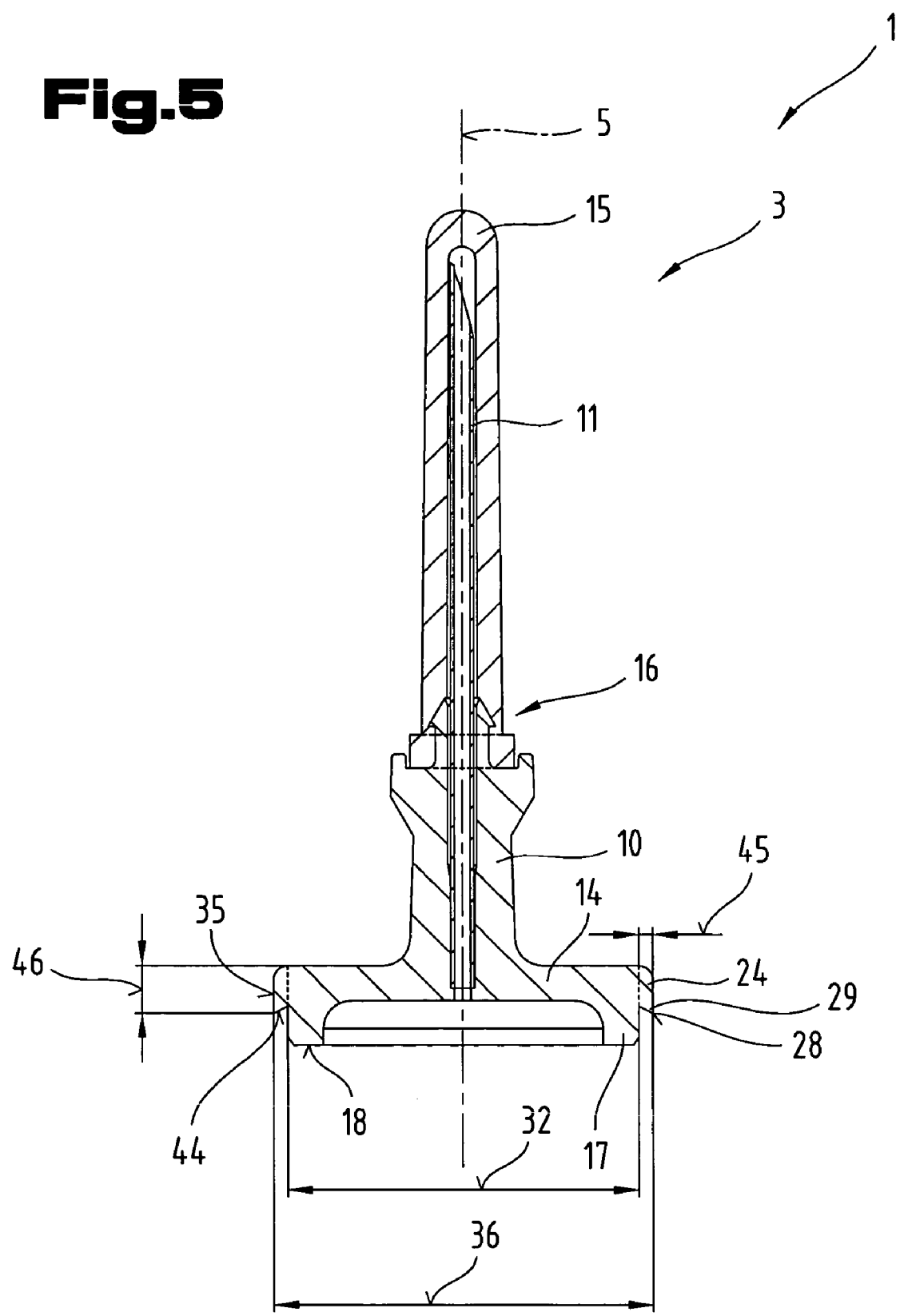
FIG. 5 shows another design of a holding part on a holder for the cannula for assembling the holding device proposed by the invention with the receiving vessel illustrated in FIG. 6.
Figure 6:
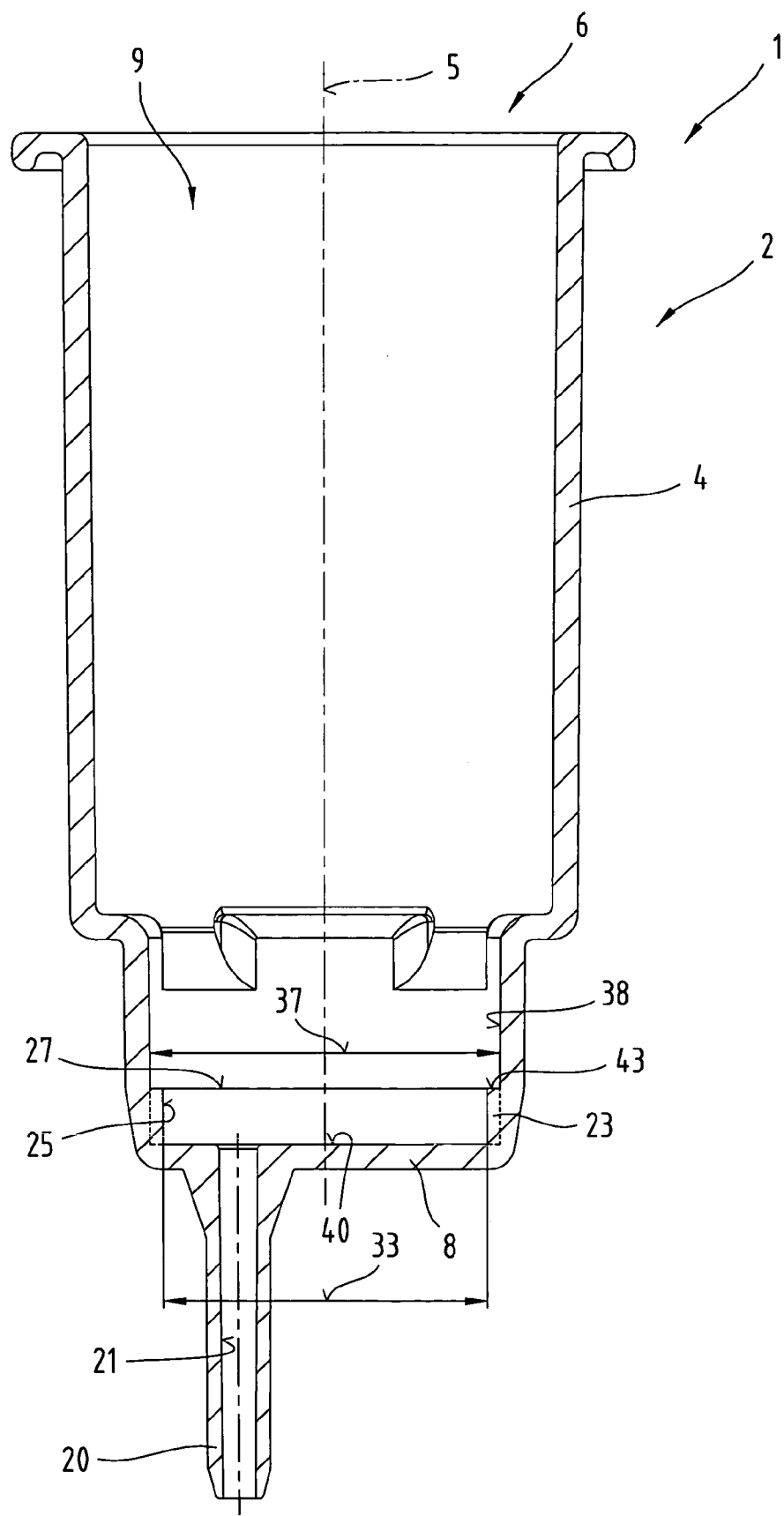
FIG. 6 shows another design of a holding part on a receiving vessel for assembling the holding device proposed by the invention, with the holder for the cannula illustrated in FIG. 6.

FIGS. 5 and 6 illustrate another and optionally independent embodiment of the holder 3 and the receiving vessel 2 for assembling the holding device 1 but in a position separated from one another and to avoid unnecessary repetition, reference may be made to the more detailed description given above with reference to FIGS. 1 to 4. The same parts are denoted by the same names and the same reference numbers as those used in connection with FIGS. 1 to 4.

The diagrams of FIGS. 5 and 6 basically correspond to the embodiment of the holder 3 and receiving vessel 2 illustrated in FIGS. 2 and 3. The difference between these embodiments lies in the design of the two connecting parts 23 and 24 and the description below will concentrate on these differences only.

The first connecting part 23 of the receiving vessel 2 in this case incorporates the boundary surface disposed parallel with the longitudinal axis 5. By contrast with FIG. 3, another boundary surface 43 is provided in this case, disposed parallel with the plane 27 extending perpendicular to the longitudinal axis 5. Consequently, on the sides facing the receiving chamber 9, the first connecting part 23 is bounded by the boundary surfaces 24, 43, which in this case extend at a right angle to one another, and by a tubular component joined to the receiving vessel 2 or constituted by it. The internal width 33 in the region of the boundary surface 25 is thus the same as or bigger than the external dimension 32 of the collar 17.

The other connecting part 24 on the support part 14, illustrated in a simplified fashion, projects out from the external boundary of the collar 17 as described in detail above and, as viewed in cross section in the direction of the longitudinal axis 5, overlaps with the first connecting part 23, in which case the external dimension 36 in the region of the external boundary surface 35 again more or less corresponds to the internal clearance width 37 of the receiving vessel 2 in the wall region adjoining the first connecting part 23 in the direction towards the open end 6.

In the embodiment illustrated here, means are provided for directing the energy 29 but, unlike the embodiments illustrated in FIGS. 1 to 4, not in the region of the first connecting part 23, but in the region of the second connecting part 24.

Another boundary surface 44 is provided, inclined at an angle to the plane 27 extending perpendicular to the longitudinal axis 5, and the inclination, starting from the outer periphery of the second connecting part 24 is directed towards the support 10 for the cannula 11. The two boundary surfaces 35, 44 terminate in the body edge 28 and thus form the means for directing the energy 29 for the common joining process. When the holder 3 is in the position illustrated with the cannula 11 at the top of the diagram, the boundary surface 44 extends down from the support part 14 towards the outer boundary surface 35 of the connecting part 24. The two converging boundary surfaces 35, 44 subtend an angle which is equal to or smaller than 90°.

Naturally, however, it would also be possible to omit the collar 17, as described in connection with FIG. 4 above, and instead provide only the connecting part 24 with the boundary surfaces 35, 44 on the support part 14, in which case the spacing elements 42, not illustrated, may also be provided as an option.

The two connecting part 23, 24 are preferably provided in the form of tubular components, the thickness 45 of which as measured in the direction perpendicular to the longitudinal axis 5 is more or less between 0.5 mm and 2.0 mm, preferably 1.0 mm. The height extension 39 of the first connecting part 23 may be between 0.2 mm and 2.0 mm. Another height extension 46 of the second connecting part 24 in the direction towards the longitudinal axis 5 may be between 1.0 mm and 4.0 mm.

The energy directing means 29 and the means forming it may also be provided on both of the connecting parts 23, 24, should this be necessary to guarantee a simple and above all reliable joining process.

As also illustrated in a simplified fashion in FIG. 1, at least one stop element 47 for a sample tube, not illustrated, on the jacket portion 4 is provided inside the receiving chamber 9 in the region of the section of the holder 10 facing the open end 6 of the receiving vessel 2. It is preferable to distribute several of these stop elements 47 around the periphery, in which case they will be dimensioned and positioned in such a way that when the sample tube is inserted, in particular a blood sample tube, the force applied as a result in the direction of the longitudinal axis is not introduced into the holder 3 or its support 10 on full insertion but, instead, is supported beforehand on the stop elements 47 so that any associated force is transmitted to the jacket portion 4 of the receiving vessel 2. These stop elements 47 are indicated in a simplified fashion in the region of the offset wall part of the jacket portion 4. The design and number of stop elements may be freely selected and will depend on the geometric shape of the sample tube. This sample tube is usually supported in the region of the cap of the closure device.

In the region of the retaining part 20, FIG. 4 also shows a simplified illustration with a hose 48 pulled onto it, as described above in connection with a blood bag, or a similar application. This hose 48 communicates with the interior of the bag or some other receiving vessel, thereby enabling samples of the contents to be taken. To this end, a sample tube is inserted into the receiving chamber 9 of the receiving vessel 2 until the cannula 11 penetrates the sealing device, not illustrated, in a known manner, thereby establishing a flow connection from the hose 48, via the flow passage 21, connecting passage 22 and flow orifice in the cannula 11 through to the sample chamber of the sample tube. To make it easier to draw off the sample, the sample chamber of the sample tube is preferably placed at a pressure slightly below the usual ambient pressure and in particular is evacuated.

Figure 7:
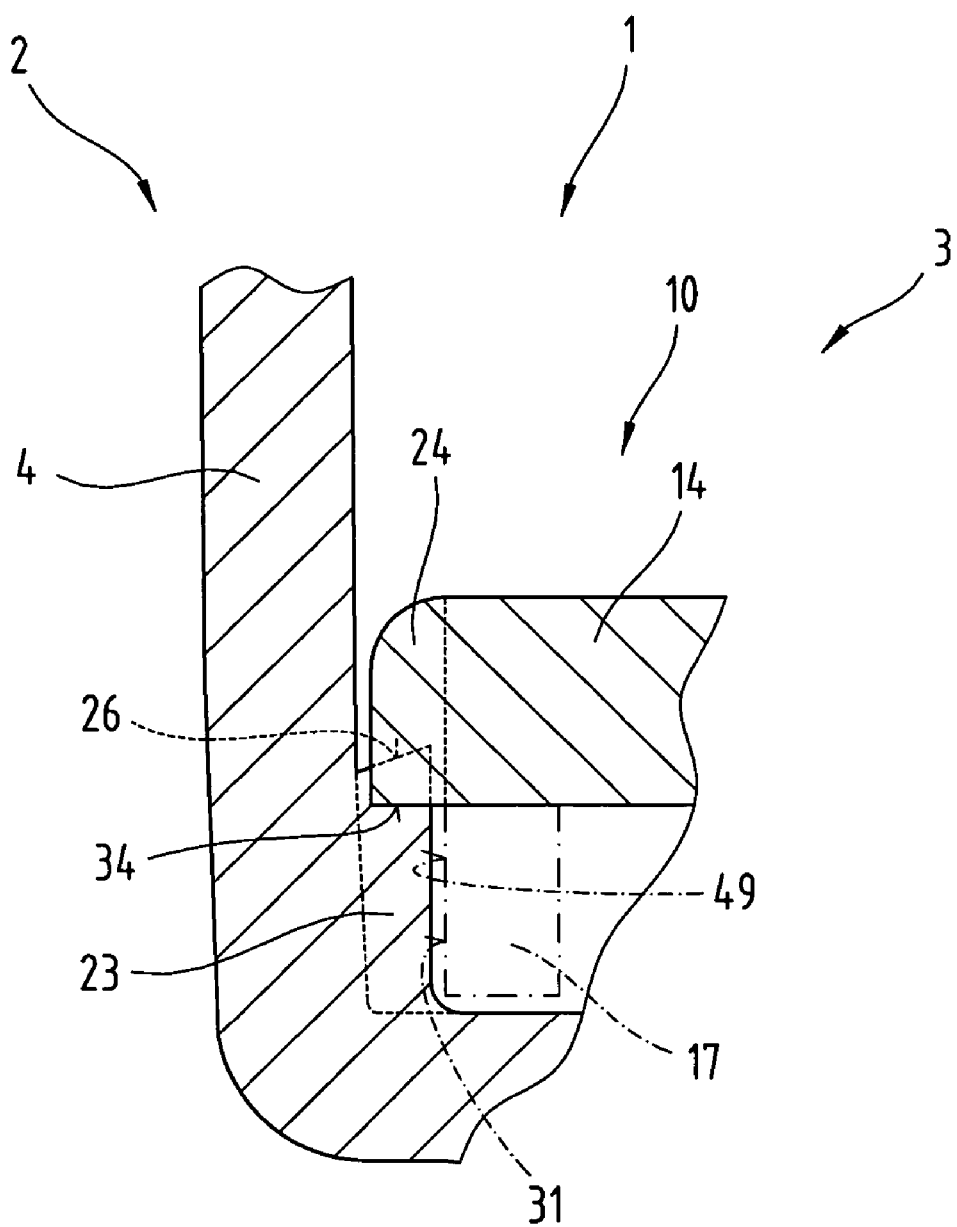
FIG. 7 is a simplified, schematic diagram on a very much enlarged scale showing a side view in section of one possible connecting region in the mutually connected position, although the weld seam is not illustrated.

FIG. 7 provides a simplified illustration of a detail of the connecting region between the receiving vessel 2 and the holder 3 in the region of the mutually facing connecting parts 23, 24, although the weld seam has been left out in order to retain better clarity and thus show the support part 14 in its relative end position with respect to the jacket portion 4 of the receiving vessel 2. The two mutually facing boundary surfaces 26, 34 of the connecting parts 23, 24 more or less completely form the cross section of the weld seam 41, not illustrated, in the plane 27 extending perpendicular to the longitudinal axis 5. The join here is made exclusively in the region of the mutually facing boundary surfaces 26, 34.

Also indicated in dotted-dashed lines in FIG. 7 is the collar 17 described above, with its delimiting ends facing the connecting part 23 and a part region of the delimiting ends 31 form an additional connecting region 49 between the connecting part 23 and the support 10 or its collar 17.

The exclusive connection between the two boundary surfaces 26, 34 is obtained by the disc-shaped support part 14 with the connecting part 24 disposed on it for example, as illustrated in FIG. 4.

The additional connection in the connecting region 49 between the collar 17 and a part section of the boundary surface 25 of the connecting part 23 may be obtained as illustrated in the diagrams of FIGS. 1 to 3. In any event, care must be taken to ensure that a gas-tight and liquid-proof joint is obtained between the mutually facing connecting parts 23, 24 at a distance from the front wall 8, in which case the joint is preferably made by one of the thermal joining processes described above.

As an alternative, however, it would also be possible to produce a gas-tight and liquid-proof joint between these two components in the region of the mutually facing connecting parts 23, 24 using a special bonding process, in which case care must also be taken to ensure that the joint region is gas-tight and liquid-proof. Likewise, however, any migration of gases, in particular air or steam, must also be reliably prevented.

For the sake of good order, it should be pointed out that in order to provide a clearer understanding of the structure of the holding device, it and its constituent parts are illustrated to a certain extent out of scale and/or on an enlarged scale and/or on a reduced scale.

The objectives underlying the independent solutions proposed by the invention may be found in the detailed description.

Above all, the individual embodiments of the subject matter illustrated in FIGS. 1, 2, 3; 4; 5, 6; 7 may be construed as independent solutions proposed by the invention in their own right. The objectives and associated solutions may be found in the detailed descriptions of these drawings.

What is claimed is:

1. Holding device (1) for assembling a medical device, which holding device (1) comprises
   (a) a receiving vessel (2) comprising
      (1) a jacket portion (4) with a longitudinal axis (5) and having an open end and
      (2) a front wall (8) closing an end (7) of the receiving vessel opposite the open end (6) and
      (3) the jacket portion (4) and front wall (8) defining a receiving chamber (9),
   (b) a first connecting part (23) disposed close to the front wall (8) on the jacket portion (4), projecting in the direction towards the longitudinal axis (5) and extending continuously around the periphery,
   (c) a retaining part (20) connected to the front wall (8) of the receiving vessel (2) and projecting therefrom in a direction remote from the jacket portion (4), the retaining part (20) being arranged eccentrically with respect to the longitudinal axis (5) and defining a flow passage (21),
   (d) a cannula (11) having one end (12) facing the front wall (8) of the receiving vessel (2) and an opposite end (13) facing the open end (6) of the receiving vessel (2), the cannula (11) defining a flow-through bore,
   (e) a holder (3) for the cannula (11), the holder (3) comprising
      (1) a support part (14) with a periphery facing the jacket portion (4) of the receiving vessel (2),
      (2) a support (10) holding the cannula (11) in a fixed position in a gas-tight and liquid-proof manner, the opposite end (13) of the cannula (11) projecting beyond the support (10), (3) the support part (14) of the holder (3) and the front wall (8) of the receiving vessel (2) defining a connecting passage (22) therebetween, the connecting passage connecting the flow passage of the holding part (20) with the flow-through bore of the cannula (11), and
(f) a second connecting part (24) extending continuously around the periphery of the support part (14) and designed to connect to the first connecting part (23) of the receiving vessel,
(g) means on at least one of the connecting parts (23, 24), said means being designed as an energy directing means (29) for providing a continuous circumferential gas-tight and liquid-proof joint between the holder (3) and the receiving vessel (2) and
(h) a selectively openable valve arrangement disposed between the connecting passage (22) and the receiving chamber (9), the valve arrangement comprising (1) a hose valve (15) disposed between the cannula (11) and the receiving chamber (9).

2. Holding device (1) as claimed in claim 1, wherein the energy directing means (29) is provided in the form of converging boundary surfaces (25, 26, 34, 35, 43, 44) terminating in a body edge (28).

3. Holding device (1) as claimed in claim 2, wherein the boundary surfaces (25, 26, 35, 44) subtend an angle equal to or smaller than 90°.

4. Holding device (1) as claimed in claim 2, wherein one of the boundary surfaces (25, 35) of the energy directing means (29) extends parallel with the longitudinal axis (5).

5. Holding device (1) as claimed in claim 2, wherein the other boundary surface (26, 44) of the energy directing means (29) is inclined at an angle to a plane (27) extending perpendicular to the longitudinal axis (5).

6. Holding device (1) as claimed in claim 1, wherein the energy directing means (29) is disposed on the first connecting part (23).

7. Holding device (1) as claimed in claim 5, wherein the inclined boundary surface (26) on the first connecting part (23) is inclined at an angle, starting from the jacket portion, (4) in the direction towards the longitudinal axis (5) and a distance from the front wall (8) increases as the distance from the jacket portion (4) in the direction towards the longitudinal axis (5) increases.

8. Holding device (1) as claimed in claim 1, wherein the first connecting part (23) on the receiving vessel (2) is a hollow cylindrical body and is moulded onto the jacket portion (4).

9. Holding device (1) of claim 1, wherein the second connecting part (24) extends around an outer periphery of the support part (14).

10. Holding device (1) as claimed in claim 1, wherein the second connecting part (24) constitutes the support part (14).

11. Holding device (1) of claim 1, wherein the energy directing means (29) is disposed on the second connecting part (24).

12. Holding device (1) as claimed in claim 11, wherein one of the boundary surfaces (43) extends at an angle to the plane (27) extending perpendicular to the longitudinal axis (5) and the inclination is directed from the outer periphery of the second connecting part (24) in the direction towards the support (10) for the cannula (11).

13. Holding device (1) as claimed in claim 1, wherein a collar (17) of a circular shape in particular is provided on the support part (14), which projects from the support part (14) in the direction away from the support (10) for the cannula (11).

14. Holding device (1) as claimed in claim 13, wherein an end surface (18) of the collar (17) is disposed at a distance from the front wall (8) of the receiving vessel (2) in the mutually connected position.

15. Holding device (1) as claimed in claim 1, wherein, when the components to be connected are in the de-moulded or loose state, the two connecting parts (23, 24) overlap with one another as viewed in cross section in the direction of the longitudinal axis (5).

16. Holding device (1) as claimed in claim 13, wherein a height (30) of the collar (17) projecting beyond the second connecting part (24) in the direction parallel with the longitudinal axis (5) is shorter than a height extension (39) of the first connecting part (23) in the same direction.

17. Holding device (1) as claimed in claim 13, wherein the collar (17) has an external dimension (32) which is the same as or slightly smaller than an internal clearance width (33) of the first connecting part (23).

18. Holding device (1) as claimed in claim 1, wherein at least one spacing element (42) is provided on the support part (14) projecting from it in the direction of the longitudinal axis (5) on the side remote from the support (10).

19. Holding device (1) as claimed in claim 1, wherein the peripheral gas-tight and liquid-proof joint between the two connecting parts (23, 24) is a weld seam.

20. Holding device (1) as claimed in claim 19, wherein the weld seam is produced by a thermal welding process selected from the group consisting of ultrasound welding, high-frequency welding or vibration welding.

21. Holding device (1) as claimed in claim 1, wherein the receiving vessel (2), the holder (3) and the connecting parts (23, 24) are made from a plastic material.

22. Holding device (1) as claimed in claim 21, wherein the plastic material is selected from the group consisting of polypropylene (PP), polystyrene (PS), polycarbonate (PC).

23. Holding device (1) as claimed in claim 1, wherein the retaining part (20) is designed as a Luer cone on at least certain regions of its external surface.

24. Holding device (1) as claimed in claim 1, wherein the retaining part (20) is of a tubular shape at its external surface, at least in certain regions.

25. Holding device (1) as claimed in claim 1, wherein at least one stop element (47) for a sample tube on the jacket portion (4), which can be inserted in the receiving chamber (9), is provided in the receiving chamber (9) in the region of the portion of the holder (10) facing the open end (6) of the receiving vessel (2).

* * * * *